US008702567B2

(12) United States Patent
Hu et al.

(10) Patent No.: US 8,702,567 B2
(45) Date of Patent: Apr. 22, 2014

(54) PRODUCTS AND METHODS FOR MOTOR PERFORMANCE IMPROVEMENT IN PATIENTS WITH NEURODEGENERATIVE DISEASE

(76) Inventors: Nicholas S. Hu, Rowland Heights, CA (US); Stephen Grill, Elkridge, MD (US)

( * ) Notice: Subject to any disclaimer, the term of this patent is extended or adjusted under 35 U.S.C. 154(b) by 1083 days.

(21) Appl. No.: 12/647,446

(22) Filed: Dec. 26, 2009

(65) Prior Publication Data

US 2010/0100013 A1 Apr. 22, 2010

Related U.S. Application Data

(63) Continuation-in-part of application No. 11/742,840, filed on May 1, 2007, now abandoned.

(60) Provisional application No. 60/796,582, filed on May 1, 2006.

(51) Int. Cl.
*A63B 71/00* (2006.01)
*A61B 5/103* (2006.01)
*A61B 5/117* (2006.01)

(52) U.S. Cl.
USPC ............................................... 482/8; 600/595

(58) Field of Classification Search
USPC .............. 482/1, 3–9, 51, 54, 66–69; 434/247, 434/255; 600/300, 587, 595; 135/65, 67; 297/5–6; 280/87.021, 87.051
See application file for complete search history.

(56) References Cited

U.S. PATENT DOCUMENTS 5,314,391 A * 5/1994 Potash et al. ..................... 482/7
5,494,049 A 2/1996 Rischbieth
5,575,294 A 11/1996 Perry et al.
5,833,549 A * 11/1998 Zur et al. ..................... 473/199
5,921,890 A 7/1999 Miley
6,498,859 B2 * 12/2002 Kuerti et al. ................. 381/361
6,645,126 B1 11/2003 Martin et al.
6,704,603 B1 3/2004 Gesotti
6,717,170 B2 4/2004 Worner
6,723,698 B2 4/2004 Rueger et al.
(Continued)

FOREIGN PATENT DOCUMENTS

WO 2008058567 A1 5/2008
WO 2009051356 A2 4/2009

OTHER PUBLICATIONS

Frenkel-Toledo, S et al., "Treadmill Walking as an External Pacemaker to Improve Gait Rhythm and Stability in Parkinson's Disease", Movement Disorders 20(9):1109-1114, 2005. Movement Disorder Soc.

(Continued)

*Primary Examiner* — Oren Ginsberg
(74) *Attorney, Agent, or Firm* — August Law, LLC; George Willinghan

(57) ABSTRACT

Systems and methods are provided to improve the gait performance of subjects with neurodegenerative disease movement disorders, injuries, surgical wounds, athletic performance objectives, or combinations thereof through feedback-enhanced training A subject walks, jogs or runs on a surface with the use of an assistive walking device such as a walker, cane, rollator or railings. Attached to the assistive walking device is a distance sensor and processing unit that detects, measures, and evaluates certain gait characteristics and delivers feedback to the subject. The subject is trained to exhibit desirable gait characteristics such as stride length, heel-toe motion, cadence, pace and the like.

29 Claims, 14 Drawing Sheets

(56) References Cited

U.S. PATENT DOCUMENTS

| | | | | |
|---|---|---|---|---|
| 6,733,423 | B1 * | 5/2004 | Chang | 482/54 |
| 6,882,955 | B1 * | 4/2005 | Ohlenbusch et al. | 702/160 |
| 6,930,603 | B2 * | 8/2005 | Jackson | 340/539.12 |
| 6,982,649 | B2 | 1/2006 | Blum et al. | |
| 7,024,398 | B2 | 4/2006 | Kilgard et al. | |
| 7,630,806 | B2 | 12/2009 | Breed | |
| 7,826,983 | B2 * | 11/2010 | Alwan et al. | 702/33 |
| 7,963,294 | B1 * | 6/2011 | Trout | 135/66 |
| 2004/0133249 | A1 | 7/2004 | Gesotti | |
| 2004/0193303 | A1 * | 9/2004 | Fore et al. | 700/126 |
| 2006/0028544 | A1 * | 2/2006 | Tseng | 348/62 |
| 2006/0100546 | A1 | 5/2006 | Silk | |
| 2006/0292533 | A1 * | 12/2006 | Selod | 434/247 |
| 2007/0255186 | A1 | 11/2007 | Grill | |
| 2009/0045021 | A1 | 2/2009 | Einbinder | |
| 2009/0246746 | A1 | 10/2009 | Roerdink et al. | |
| 2009/0275867 | A1 | 11/2009 | Santos-Munne et al. | |

OTHER PUBLICATIONS

Grill, S, "Postural Instability in Parkinson's Disease", Maryland Med. J. 48(4):179-181, 1999.

Protas, E, "Reducing Falls in Parkinson's Disease", International Conference on Aging, Disability and Independence, 2003 Conference Presentation.

Montoya et al., "Step-length Biofeedback Device for Walk Rehabilitation", Jul. 1994, Medical Biological Engineering and Computing, 32, 416-420.

International Searching Authority, International Search Report for related PCT Application PCT/US2010/062108, May 17, 2011.

* cited by examiner

PRODUCTS AND METHODS FOR MOTOR PERFORMANCE IMPROVEMENT IN PATIENTS WITH NEURODEGENERATIVE DISEASE

CROSS-REFERENCE TO RELATED APPLICATIONS

The present application is a continuation-in-part of abandoned U.S. application Ser. No. 11/742,840, filed May 1, 2007, which was a non-provisional claiming priority to U.S. provisional application No. 60/796,582 filed May 1, 2006. The entire disclosures of both applications are incorporated herein by reference.

FIELD OF THE INVENTION

The present invention relates to improving motor performance in subjects with neurodegenerative conditions, movement disorders, injuries, surgical wounds and athletic performance objectives.

BACKGROUND OF THE INVENTION

Neurodegenerative diseases, such as Guillain-Barre syndrome, Huntington's disease and amyotrophic lateral sclerosis (ALS), multiple sclerosis (MS) and Parkinson's Disease (PD) and injuries caused by stoke, atherosclerosis, traumatic injury from accident, and the like, afflict patients with a reduced ability of movement. Parkinson's Disease is a progressive neurodegenerative disease that causes affected individuals to move slowly and make small movements. Subjects with Parkinson's Disease display tremor, rigidity, bradykinesia and postural instability. Without the use of exteroceptive (visual or auditory) input, subjects with PD make hypometric movements (Flowers, *Brain,* 99:269-310, 1976, Klockgether & Dichgans, *Mov. Disord.,* 9:48-56, 1987) but motor performance improves with auditory or visual cues (Georgiou et al, *Brain,* 116:1575-78,1993).

The gait in subjects with PD can be described as shuffling, with short hesitant steps that are sometimes quick (festinating). Subjects with PD have difficulty initiating their gait and walk stiffly with limited arm swing. Postural instability is usually a relatively late symptom of the disease and one that is not amenable to current medical or surgical therapy (Koller et al, *Clin. Neuropharmacol,* 12:98-105, 1989), although some improvement in balance has been reported with bilateral subthalamic stimulators (Bejjani et al., *Jour. Neural. Neurosurg. Psych.* 68(5):595-600, 2000). Subjects with PD experiencing postural instability are at increased risk of falls resulting in traumatic injuries and are usually dependent on the use of assistive devices such as walkers. In one survey, subjects with PD had a yearly incidence of broken bones of 35.6% of which ⅓ were hip fractures (Pressley et al., *Neurology,* 60(1):87-93, 2003). Following hip fractures, the gait worsens and 21.9% may be fully unable to walk (Gialanella, *Minerva Med.,* 92(3):11-6, 2001). In addition, freezing and gait hesitation usually occur relatively late in the disease and can be quite debilitating even when the other symptoms of the disease are well-treated medically.

Although subjects with PD are routinely sent for physical therapy to address their gait problems, the efficacy is not well documented. Furthermore, the methods used vary from center to center and have not been subjected to rigorous scientific investigation. Weight-supported treadmill training, a technique in which the subject walks on a treadmill with partial body weight support through an overhead harness as well as a pelvic belt has been found to improve gait stride length and speed in persons with strokes (Miyai et al., *Arch. Phys. Med. Rehabil.* 81:849-52, 2000) and these benefits may be long-lasting (Miyai et al., *Arch. Phys. Med. Rehabil.,* 83:1370-3, 2002). The mechanism for the improvement is unknown. A portion of the improvement with treadmill training in PD may be due to aerobic conditioning since that seems to be a factor when applied to stroke patients (Macko et al. *Stroke,* 28:326-330, 1997; Macko et al, *Arch. Phys. Med. Rehab.,* 82(7):879-884, 2001). In this training in subjects with PD, the weight support may be a factor (Visintin et al, *Stroke,* 29:1122-28, 1998) in the improvement aside from any improvements resulting from more efficient energy expenditure. Frenkel-Toledo et al. (*Movement Disorders* 20(9)11109-1114, 2005) suggest that the treadmill itself may be acting as an external cue to enhance the rhythmicity of the gait of the subject with PD, but did not demonstrate any stride length improvements.

It is a common observation that subjects with PD may undergo severe "freezing" when attempting to go through doorways but may have little trouble going up stairs or when there is a repeated pattern on the floor. These visual stimuli can have large effects on a subject's gait. There is a commercially-available cane (STEPOVER WAND®) that employs a red wire as a visual stimulus or a visual aid for subjects experiencing freezing. With this device, subjects are explicitly using visual input to help improve the magnitude of their steps. It is well accepted that visual stimuli may improve gait by alleviating freezing, and in fact, there are improvements in gait in subjects with PD with visual and auditory cueing (Suteerawattananon et al, *J. Neurol. Sci.,* 219:63-69, 2004). However, the improvements with auditory cueing (using a metronome) were in cadence rather than stride length (Suteerawattananon et al., *Ibid,* 2004).

The use of the term "gait improvement," as used herein, means the alleviation of freezing and hesitation.

The short steps that subjects with PD take are one form of the hypometria they experience, and this is also present during movements of the upper extremities. With visual feedback, subjects are able to make larger limb movements, and the deficit may be due to a sensory-motor mismatch (Demerci et al. *Ann. Neurol.,* 41:781-788, 1997). That is, the kinesthetic signal may be "felt" as indicating the subject has made an adequately-sized movement even though he has not. Subjects with PD perceive distances to be shorter than control subjects when they use kinesthesia rather than vision. Subjects with PD often feel they are speaking at a normal volume even though they may be severely hypophonic (Marsden, *Neurology,* 32:514-539, 1982), but when they are coerced into speaking louder they feel as if they are shouting (Ramig et al, *J. Med. Speech Lang. Pathol,* 2:191-209, 1994). Apparently during both limb movements and speech, subjects with PD have a feeling of performing well and do not attempt to make corrections because they do not feel any discrepancy between their motor intention and performance (motor output) as long as there is no exteroceptive feedback. Based on these ideas, improvements in speech have been achieved (the Lee Silverman Voice Treatment program). The focus is on producing a louder volume and this results in improvements in articulation as well (Ramig, *Intelligibility in Speech Disorders: Theory, Measurement and Management,* John Benjamins Pub. Co., R. Kent, ed., Amsterdam, 1992) even though articulation is not stressed during the therapy. These ideas have not been applied to physical therapies for gait.

U.S. Pat. No. 6,704,603 B1 and divisional U.S. Publication no. 2004/0133249 A1 describe a method of adaptive stimulation and an adaptive stimulator product. The '603 patent describes a control unit and method to aid in the relief of symptoms of Parkinson's disease. The device disclosed electrically stimulates a subject's muscles at a set rhythm to stimulate better movement or uses a signal to tell the subject when to take a step. Stride lengthening is not disclosed.

Since subjects with neurodegenerative disease have a greatly increased risk of suffering traumatic injuries as a result of postural instability, intervention with physical therapies and the use of assistive devices, such as canes and walkers, may be helpful in preventing these falls. Various experimental therapy methods including Body Weight Supported Treadmill Training (Miyai et al., *Ibid,* 2000, 2002), and visual and auditory cueing (Suteerawattananon et al, *Ibid,* 2004) have demonstrated some improvement in gait parameters. However, there are no standardized physical therapeutic modalities that lead to improvement in gait or postural stability. There is a need in the art for improving the gait stride length, gait shape, and gait pace of a subject, as well as improving general postural stability in subjects with neurodegenerative disease.

Subjects recovering from surgeries to the lower body, such as total hip replacement, total knee replacement, arthroscopic surgery and prosthetic device implantation as well as subjects recovering from traumatic injuries often exhibit less-than-ideal gaits. That is, the gait of the patient consists of a short stride length, a flat-footed shuffling motion, an unstable step that wavers laterally from the intended stepping direction or combinations thereof. Current physical therapy applied to subjects recovering from these afflictions includes practice of proper walking form and range-of-motion exercises. However, proper performance of the exercises is only ensured when a physical therapist or attending clinician is present to guide the subject. There is a need for improving the range-of-motion, gait stride length, gait shape and gait pace of a subject through guided therapy even in the absence of an attending health care provider.

Subjects, both human and animal, with aesthetic or athletic performance objectives relating to stride and gait characteristic such as optimized stride length, gait shape, cadence and the like can benefit from real-time feedback of their gait characteristics. Human performers and athletes have to rely on reviewing video of their gait after their training session to determine how they must alter their gait in the next training session to more closely reflect desired gait characteristics. Animals that are desired to have certain aesthetic or athletic performance objectives relating to their gait must rely on human trainers to provide feedback of the adequacy of their gait characteristics during the training session. There is a need for real-time feedback to subjects of the adequacy of their gait characteristics in meeting desired gait characteristics without the use of a human trainer.

SUMMARY OF THE INVENTION

The present invention is directed to products and methods to improve gait performance in subjects with neurodegenerative conditions, movement disorders, injuries, surgical wounds, athletic performance objectives and combinations thereof.

Exemplary embodiments in accordance with the present invention use feedback methods during walking, running, and variations of walking and running, for example on a treadmill, with a rollator, or other assistive walking device, to train the gait in subjects with afflictions such as neurodegenerative diseases, movement disorders, injuries, surgical wounds, athletic performance objectives, or combinations thereof to embody certain characteristics. These characteristics may include stride length, heel-toe motion, stepping cadence, pace, stride shape and the like.

The present invention includes a walking surface and an assistive walking apparatus which is available to help the subject maintain stability while standing, walking, jogging, running, or variations thereof. For example, on a walking surface such as the ground, the subject may use an assistive walking apparatus in the form of a walker, rollator, crane, crutch, wheelchair, or variations thereof; on a walking surface such as a treadmill surface, the subject may use an assistive walking apparatus in the form of railings along the treadmill surface. Furthermore, the present invention includes a gait training system that the subject himself or a clinician, therapist, nurse, trainer, or other attendant to the subject attaches to the assistive walking apparatus. In one embodiment, the range of detection of a distance sensor is positioned to be orthogonal to the plane of motion of the subject's foot during a step. In addition, the range of detection is positioned to detect the presence of a desired characteristic of each step. The distance sensors measure distance using electromagnetic radiation, such as infrared light and radar, or sonic waves, such as ultrasound.

Crossing of the target beam by a portion of the subject is determined by comparing the data generated by the distance sensor, which measures the distance to the closest object in its line of detection. A calibration dial in a processing unit controlling the distance sensor is used to set a threshold distance. The threshold distance is determined to reflect the lateral variability of the subject's gait or the width of the assistive walking apparatus, whichever is greater. The system interprets any distance greater than this threshold as an uninterrupted target beam. The system interprets any distance smaller than this threshold as the subject's leg or foot interrupting the target beam. This comparison is done by an electronic circuit, microprocessor, computer, or other suitable components. Positive auditory feedback of crossing the target beam is also generated by an electronic circuit, microprocessor or computer and actuated through electro-acoustic transducers such as loudspeakers, earphones, headphones, piezoelectric speakers and variations thereof. Positive visual feedback of crossing the target beam is also generated by an electronic circuit, microprocessor or computer and actuated through light emitting diodes, LCD displays, computer displays, gauges, lights, paper printout, and variations or combinations thereof.

Exemplary embodiments of the present invention include a method for evaluating the subject's performance of the heel-toe motion. For example, the range of detection of the distance sensor is set to detect the presence of a heel-toe motion in the step and is positioned a distance above the walking surface. If the subject does not perform the heel-toe motion and steps in a flat-footed fashion, the subject's foot will not cross into the range of detection and no positive auditory and/or visual feedback is given for that step. The processing unit collects and evaluates data accordingly.

Exemplary embodiments of the present invention include a method for training the subject to perform the heel-toe motion with each step. The range of detection of the distance sensor is set to detect the presence of a heel-toe motion in the step and is positioned a distance above the walking surface. In this embodiment, when the subject does not perform the heel-toe motion and steps in a flat-footed fashion, the subject's foot will not cross the target beam and no positive auditory and/or visual feedback is given for that step. The subject is instructed to modify each successive step so that each step elicits positive feedback.

Exemplary embodiments of the present invention include a method for evaluating the subject's stride length. The range of detection of the distance sensor is set to detect a minimum stride length and is positioned a certain distance away from the subject along the intended walking path. When the subject does not step the minimum length, the subject's foot will not cross the target beam and no positive auditory and/or visual feedback is given for that step. The processing and control unit collects data accordingly.

Exemplary embodiment of the present invention includes a method for training the subject to exhibit a minimum stride length. The range of detection of the distance sensor is set up to detect a minimum stride length and is hence positioned a certain distance away from the subject along the intended walking path. When the subject does not step the minimum length, the subject's foot will not cross the target beam and no positive auditory and/or visual feedback is given for that step. However, the range of detection is set to detect both the presence of a heel-toe motion in the step as well as a minimum stride length and is positioned a distance above the walking surface as well as a certain distance away from the subject along the intended walking path. When the subject both performs the desired heel-toe motion as well as strides the minimum length, the subject's foot crosses the target beam and a positive auditory and/or visual feedback is given in the form of a tone and/or light. The subject is instructed to modify each successive step so that each step elicits positive feedback.

Exemplary embodiments of the present invention include a method for evaluating and training the cadence of the subject's gait. The range of detection of the distance sensor is placed at a distance near enough to the subject and close enough to the walking surface that every step will cross it. The electronic circuit, microprocessor, or computer used to process data from the distance sensor and to generate the feedback signals sent to the audio and visual actuators may additionally be programmed to time the period between successive steps and provide negative auditory and/visual feedback when the cadence is not within a desired window. One form of auditory or visual feedback, such as a low frequency beep or yellow light, is generated to signal that the subject's cadence is too slow, and another form of auditory or visual feedback, such as a high frequency beep or red light, is generated to signal that the subject's cadence is too fast. The processing unit collects data accordingly, or if the subject is being trained, the subject is instructed to modify his cadence to avoid eliciting the negative feedback.

Exemplary embodiments of the present invention include a method for evaluating and training the minimum pace of the subject's gait. The range of detection off the distance sensor is placed at a distance from the subject correlating to the desired stride length every step of sufficient length will cross it. The electronic circuit, microprocessor, or computer used to process data from the distance sensor and to generate the feedback signals sent to the audio and visual actuators may additionally be programmed to divide the minimum distance of each stride that crosses the target beam by the time between strides to determine the pace of the subject's gait and provide negative auditory and/visual feedback when the pace is not within a desired window. One form of auditory or visual feedback, such as a low frequency beep or yellow light, is generated to signal that the subject's pace is too slow, and another form of auditory or visual feedback, such as a high frequency beep or red light, is generated to signal that the subject's pace is too fast. The processing unit collects data accordingly, or if the subject is being trained, the subject is instructed to modify his pace to avoid eliciting the negative feedback.

Exemplary embodiments of the present invention include a method for evaluating and training the subject's left leg gait and right leg gait independently. The electronic circuit, microprocessor, or computer used to process data from the distance sensor and to generate the feedback signals sent to the audio and visual actuators may additionally be programmed to determine if each datum collected by the distance sensor corresponds to the subject's left or right foot. If the distance sensor is attached to the assistive walking apparatus on the subject's left side, then the a datum corresponds to a step by the left leg if the distance measured by the sensor is significantly shorter than both the calibrated threshold distance as well as the distance measured by the sensor during the previous step; the datum corresponds to a step by the right leg if the distance measured by the sensor is significantly shorter than both the calibrated threshold distance as well as the distance measured by the sensor during the previous step; and the datum corresponds to a step by the same leg that performed the previous step if the distance measured by the sensor is not significantly shorter nor significantly longer than the distance measured by the sensor during the previous step. The opposite determinations would be made if the distance sensor is attached to the assistive walking apparatus on the subject's right side.

Exemplary embodiments of the present invention include a method for evaluating and training the symmetry of the subject's gait. Since the subject's left and right legs may be evaluated independently, the electronic circuit, microprocessor, or computer used to process data from the distance sensor and to generate the feedback signals sent to the audio and visual actuators may additionally be programmed to compare the adequacy of the subject's left leg gait in exhibiting desired characteristics against the adequacy of the subject's right left gain in exhibiting the same characteristics. One example is to set up the gait training system to evaluate achievement of a minimum stride length. The most current datum corresponding to the left stride length may be compared to the most current datum corresponding to the right stride length. If the difference between the two lengths is greater than a certain preset tolerance, then the gait training system shall deliver negative auditory or visual feedback to indicate to the subject and persons attending to the subject that the left and right stride lengths are not sufficiently symmetrical. The processing unit collects data accordingly, or if the subject is being trained, the subject is instructed to modify his pace to avoid eliciting the negative feedback. Using similar methods, symmetry in other characteristics of gait, such as performance of the heel-toe motion, stepping speed, and the like may be evaluated and trained.

Exemplary embodiments of the present invention include a method for evaluating and reducing the lateral wavering of the subject's gait. Since the subject's left and right legs may be evaluated independently, the electronic circuit, microprocessor, or computer used to process data from the distance sensor and to generate the feedback signals sent to the audio and visual actuators may additionally be programmed to compare the distance measured by the distance sensor of the left or right leg when it crosses the target beam during the current step to the distance measured by the distance sensor of the same leg when it crossed the target beam during the previous step. If the difference between these two distances shows that the two distances are significantly different, as determined by a preset tolerance, then the gait training system shall deliver negative auditory or visual feedback to indicate to the subject and persons attending to the subject the detection of wavering in the subject's gait. The processing unit collects data accordingly, or if the subject is being trained, the subject is instructed to modify his gait to avoid eliciting the negative feedback.

The present invention includes the placement of distance sensors in positions so that other parts of the subject's leg, such as the knee, shin, or thigh, cross the target beam of the distance sensor to trigger feedback on the subject's gait characteristics. In addition, the present invention includes the simultaneous placement of multiple distance sensors in same or varying positions to make evaluate and provide feedback on multiple gait characteristics at the same time.

DETAILED DESCRIPTION OF THE INVENTION

Figure 1:
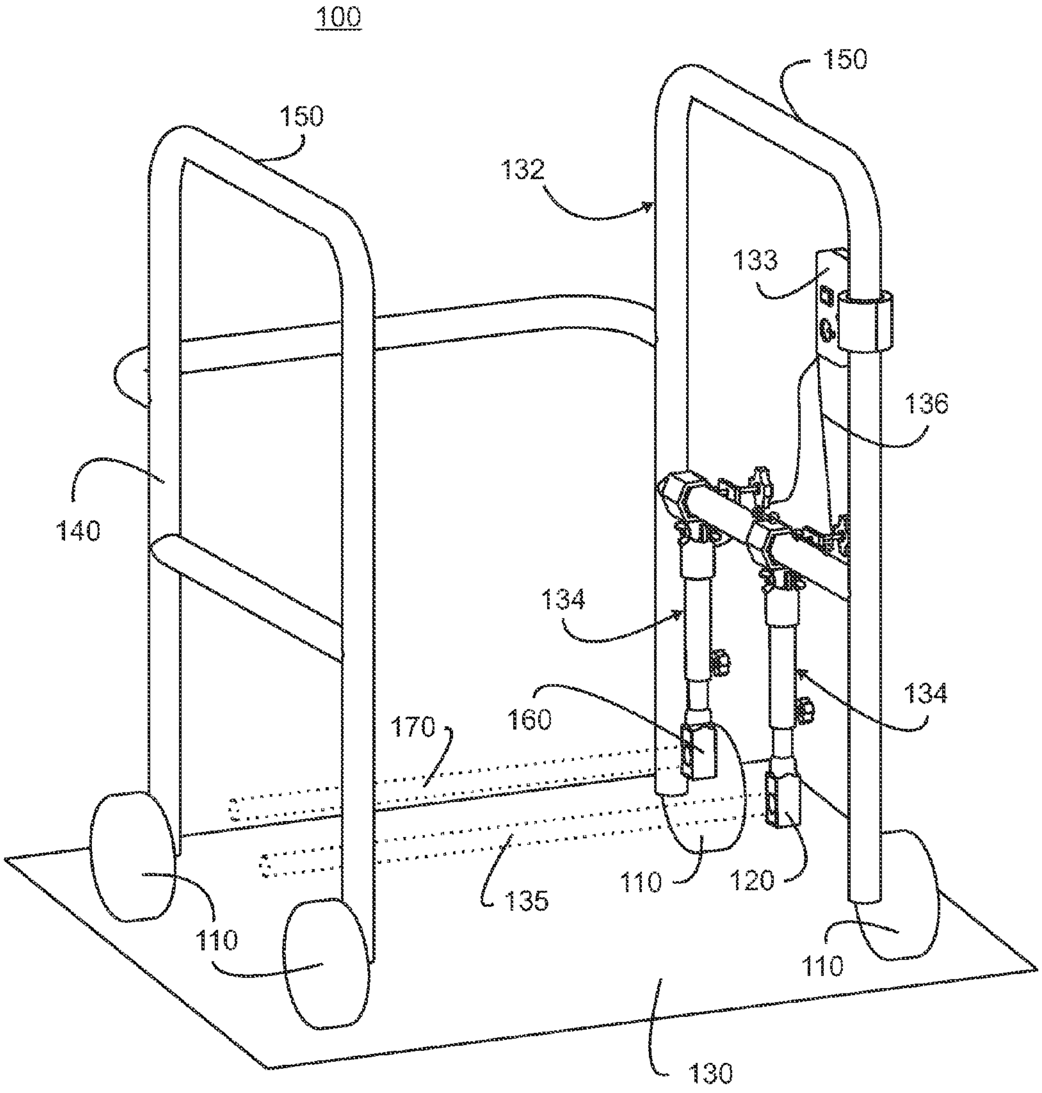
FIG. 1 is a back perspective view from a first side of an embodiment of a feedback-enhanced assistive walking device in accordance with the present invention.
Figure 2:
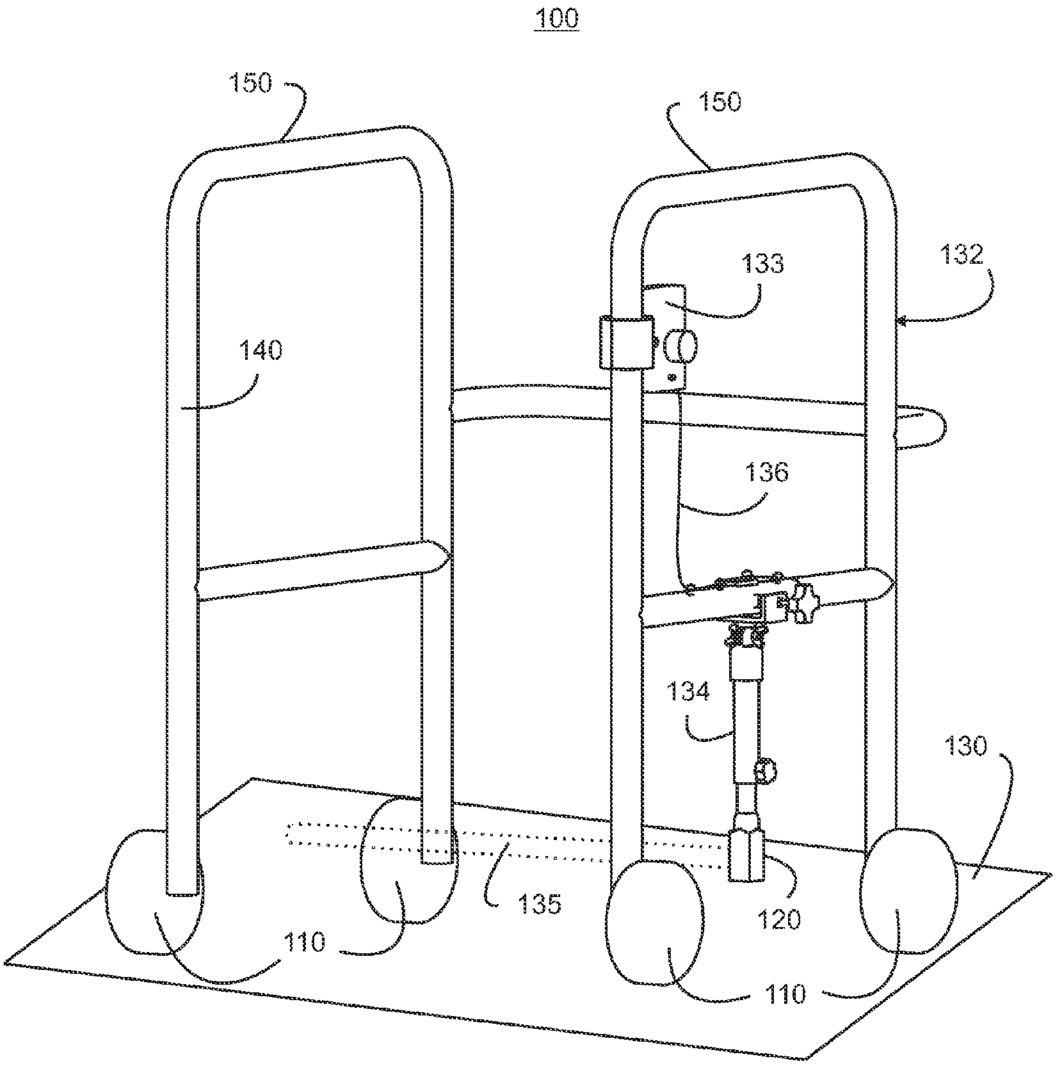
FIG. 2 is a back perspective view from a second side of an embodiment of a feedback-enhanced assistive walking device in accordance with the present invention.
Figure 3:
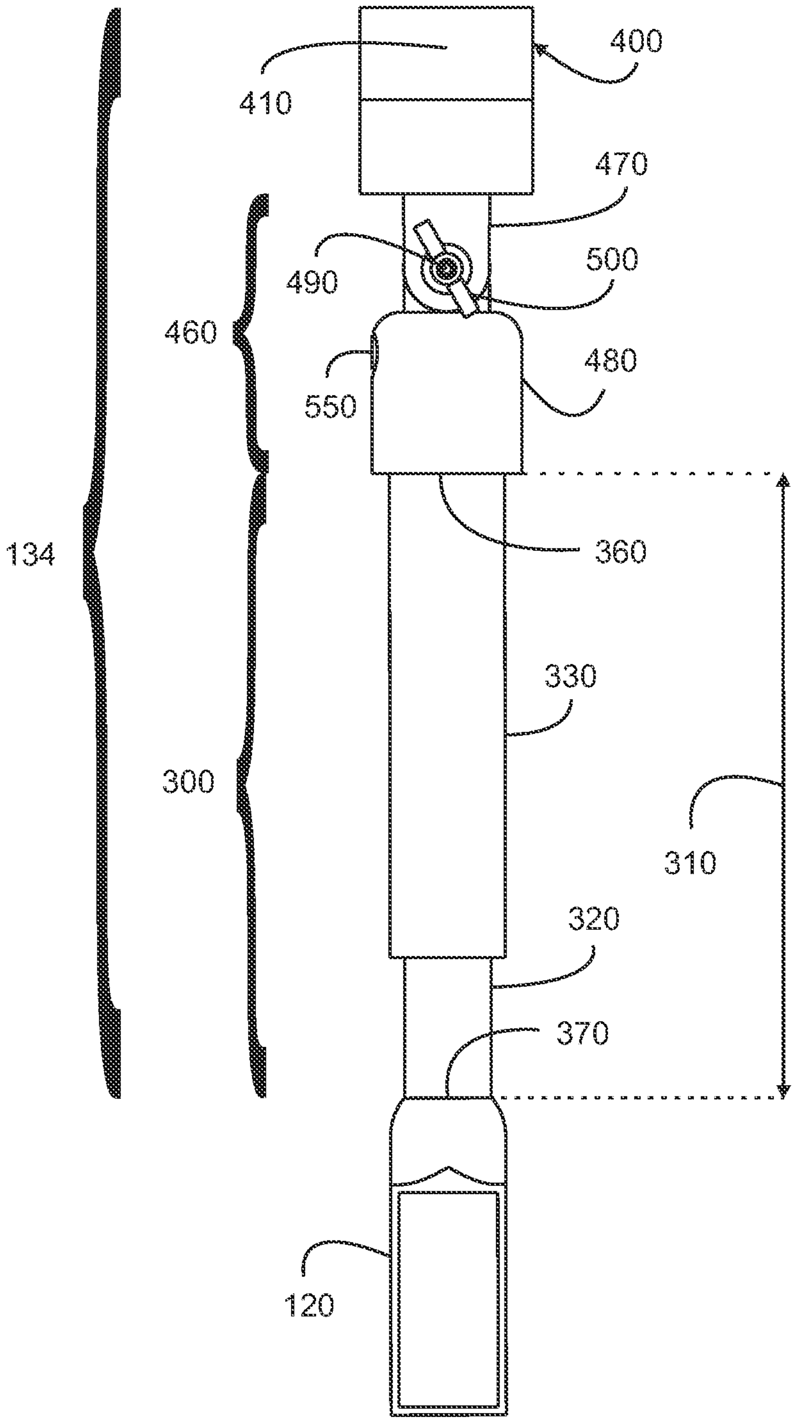
FIG. 3 is a front elevation view of an embodiment of distance sensor mount and distance sensor for use in accordance with the present invention.
Figure 4:
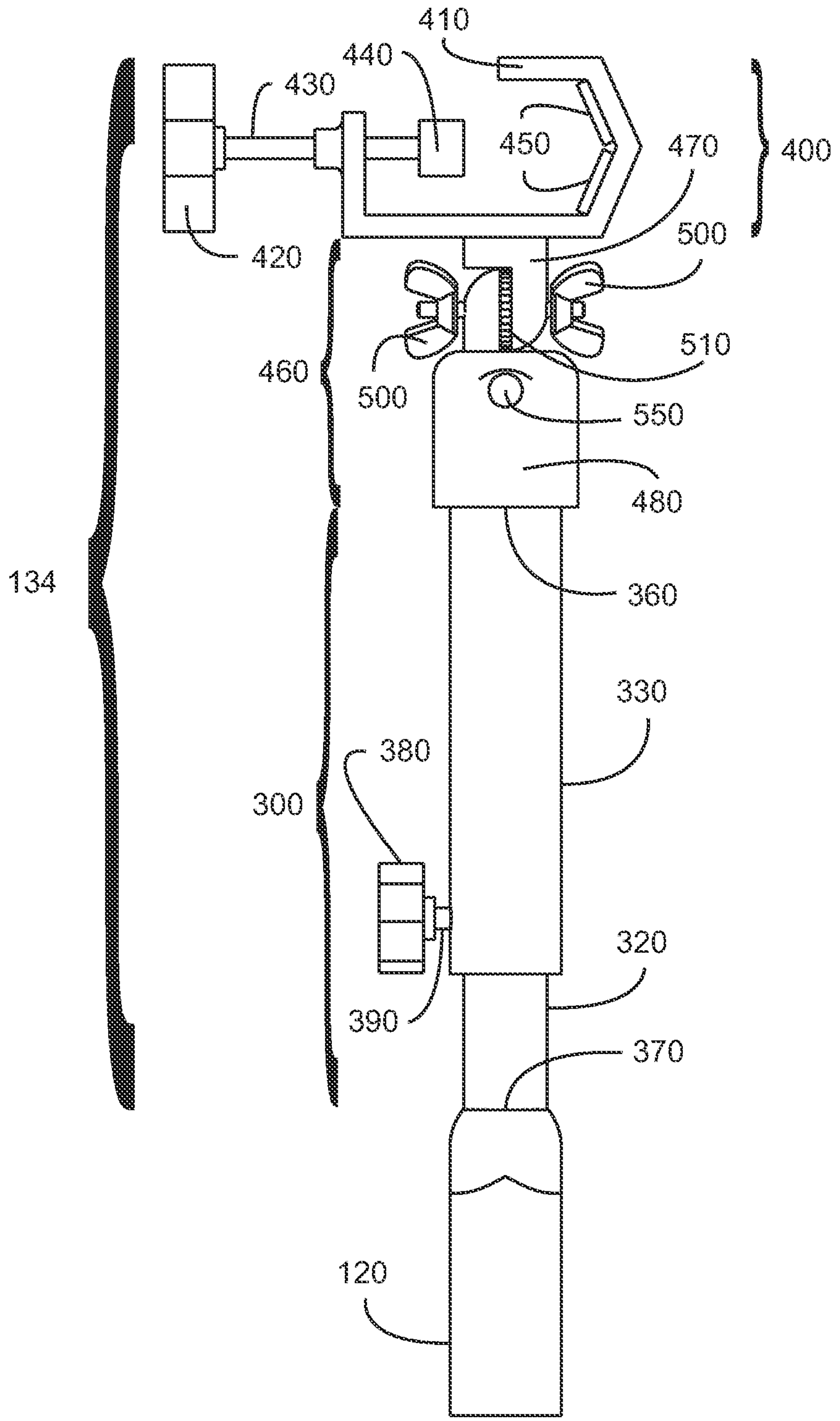
FIG. 4 is a side elevation view of the distance sensor mount and distance sensor of FIG. 3.
Figure 5:
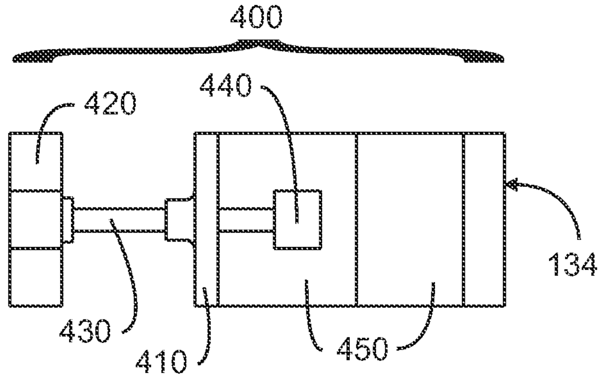
FIG. 5 is a top plan view of the distance sensor mount and distance sensor of FIG. 3.
Figure 6:
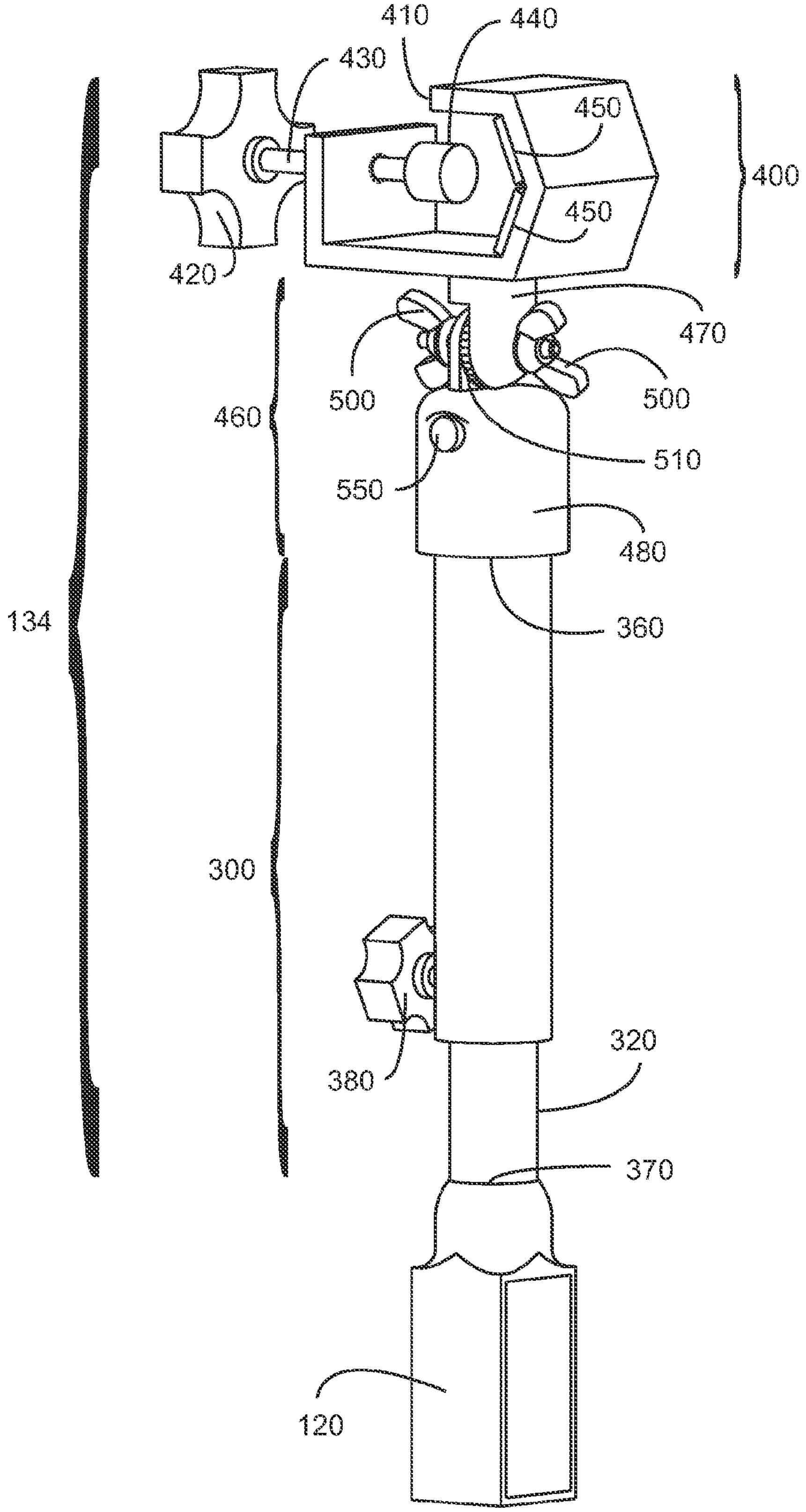
FIG. 6 is a perspective view of the distance sensor mount and distance sensor of FIG. 3.
Figure 7:
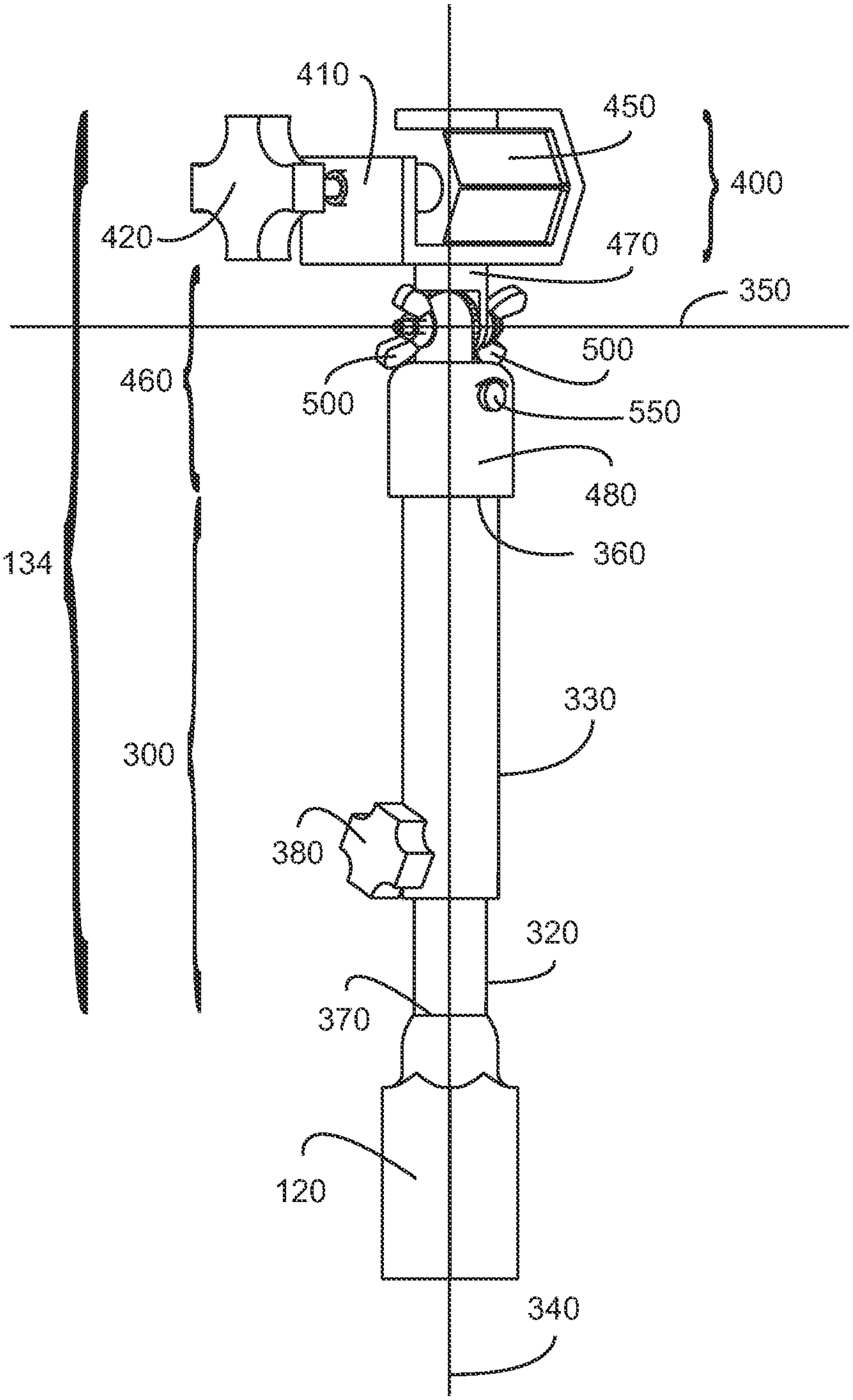
FIG. 7 is a plan view of the distance sensor mount and distance sensor of FIG. 3 with axis lines.

The present invention is directed to a system for improving movement in a subject. The movement includes a person moving by foot across a walking surface such as a floor or the ground and encompasses any type of movement by foot including walking and running Referring initially to FIGS. 1 and 2, an exemplary embodiment of a system 100 includes an assistive walking device 132 that includes a frame 140 that extends up from a walking surface 130. The frame is configured to support the subject that is moving by foot, i.e., walking or running, across the walking surface. In one embodiment, the assistive walking device 132 is a walker, a wheeled rollator, a cane or a rolling chair. In this embodiment, the walking surface is the floor or ground across which the subject moves with the assistive walking device. Therefore, the assistive walking device moves with regard to a stationary walking surface. Alternatively, the assistive walking device is stationary and the walking surface moves. In another embodiment, the assistive walking device is a treadmill and the walking surface is a moving treadmill surface of the treadmill.

In the embodiment as illustrated, the system 100 is a feedback-enhanced rollator device 100 and the assistive walking device is a rollator 132 having a tubular frame 140 that is used by a subject to provide walking assistance. The frame 140 is a three-sided frame, and the subject will grasp the frame along a pair of horizontal top rails 150 and stand generally within the three sides of the frame. Suitable rollators are known and available in the art, and any suitable rollator provides the desired walking assistance can be used. The rollator 132 also includes two or four wheels 110 that roll along the walking surface 130.

The system 100 also includes a first distance sensor 120 that is attached to any desired location along the frame 140 of the assistive walking device 132. The first distance sensor 120 can be selectively placed along any desired portion of the frame 140 and fixedly secured in that portion of the frame 140. In addition, the first distance sensor 120 can be remove from the frame 140 or moved along elements of the frame 140 without completely removing the first distance sensor 120 from the frame 140. This facilitates adjustment of the location and monitored area of the first distance sensor with respect to the assistive walking device 132 and the walking surface 130.

In one embodiment, the first distance sensor 120 includes a range of detection 135, i.e., a range over which the sensor can detect objects and determine the distance to those objects. The range of detection 135 extends along a first line, extending from the frame across the walking surface. The distance sensor can detect objects crossing into the first line within the range of detection. In addition to detecting the occurrence of an object crossing into the range of detection, the distance sensor can determine or calculate a distance from that object to the distance sensor. Therefore, the distance sensor provides two distinct measurements, object detection and distance to object measurement. In one embodiment, these objects include portions or parts of the subject that is moving by foot along the walking surface, for example, a foot, leg (upper and lower), shin, knee, hip, torso, arm, neck or head.

In one embodiment, the first distance sensor 120 is an optoelectronic distance sensing device that includes an optical light source emitting a pre-defined frequency of light along the first line and a photodetector filtered to detect the pre-defined frequency. Suitable optical light emitting sources are known and available in the art. In one embodiment, the optical light emitting source emits infrared light, for example, light having a pre-defined frequency from about 1 mm to about 750 nm. The optical light source and photodetector are aligned with the range of detection in order to emit light and to detect reflected light along the line of the range of detection.

In one embodiment, the system also includes a timing device (not shown) in communication with the optical light source and photodetector. This timing device or the necessary electrical or electronic circuitry for the timing device can be incorporated into the first distance sensor 120 or can be provided in a separate control mechanism that is in communication with the first distance sensor. The timing device measures an elapsed time for light of the pre-defined frequency to project or to be emitted from the optical light source along the first line, to reflect on the object crossing into the first line and to fall upon the photodetector. This can be used to calculate the distance of the object from the first distance sensor.

In one embodiment, the distance sensor 120 is a sonic-electric distance sensing device that includes a cyclic sound pressure generator emitting a pre-defined frequency of sound along the first line and a sonic detector configured to detect the pre-defined frequency of sound being reflected along the first line. Suitable cyclic sound pressure generators are known and available in the art. In one embodiment, the pre-defined frequency is an ultrasonic frequency of at least about 20 kHz. The cyclic sound pressure generator and sonic detector are aligned with the range of detection in order to emit sound and detect reflected sound along the line of the range of detection.

In one embodiment, the system also includes a timing device in communication with the cyclic sound pressure generator and the sonic detector. The necessary electrical or electronic circuitry for the timing device can be incorporated into the first distance sensor 120 or can be provided in a separate control mechanism that is in communication with the first distance sensor. The timing device measures an elapsed time for sound of the pre-defined frequency to project from the cyclic sound pressure generator along the first line, to reflect on the object crossing into the first line and to fall upon the sonic detector. This can be used to calculate the distance of the object from the first distance sensor.

In one embodiment, the distance sensor 120 is a radio detection and ranging device that includes a radio transmitter emitting a pre-defined frequency of radiation along the first line and a radio receiver configured to detect the pre-defined frequency of radiation. Suitable radio transmitters are known and available in the art. The radio transmitter and radio receiver are aligned with the range of detection in order to emit radiation and detect reflected radiation along the line of the range of detection.

In one embodiment, the system also includes a timing device in communication with the radio transmitter and the radio receiver. The necessary electrical and electronic circuitry for the timing device can be incorporated into the first distance sensor 120 or can be provided in a separate control mechanism that is in communication with the first distance sensor. The timing device measures an elapsed time for radiation of the pre-defined frequency to project from the radio transmitter along the first line, to reflect on the object crossing the first line and to fall upon the radio receiver. This can be used to calculate the distance of the object from the first distance sensor.

In one embodiment, the system 100 includes a second distance sensor separate from the first distance sensor. The second distance sensor is attached to the frame of the assistive walking device 132 and has a range of detection 170 extending along a second line running from the frame 140 across the walking surface 130. This second line is separate from the first line. The second distance sensor 160 is configured to detect an object crossing into the second line within the range of detection and to determine a distance from that object to the second distance sensor.

Suitable embodiments and configurations for the second distance sensor 160 are the same as for the first distance sensor 120. The first and second distance sensors can be the same type of sensor or different types of sensors, e.g., ultrasonic and infrared. In addition, both distance sensors can have the same type of associated mounting and control structures. In one embodiment, the first distance sensor and the second distance sensor comprise a unitary structure. As illustrated, the first and second distance sensors are separate structures, and the second distance sensor 160 is positioned farther from a subject using the assistive walking device. In addition the first and second ranges of detection are parallel. However, the second distance sensor 160 can be attached to any suitable location of the frame 140 of the assistive walking device 132. The second distance sensor can be positioned closer to or farther from the subject, higher up from the walking surface or lower down toward the walking surface. The second distance sensor 160 can be located on section of the frame opposite the first distance sensor such that the sensors are facing in opposite direction. In addition, the second distance sensor 160 can be positioned on the frame such that the ranges of detection are not parallel but intersect, for example at an angle of about 90 degrees. In addition to a single second distance sensor, the system 100 can include a plurality of second distance sensors each configured as discussed above for the single second distance sensor.

Although the distance sensors can be provided with a housing that is mounted directly to the frame 140 of the assistive walking device 132 using suitable mounting devices such as clamps and magnets, the system includes a distance sensor mount 134 attached to the frame 140 of the assistive walking device 132. The distance mount sensor permits adjustment of the location of distance sensors attached to the mount include spacing of the range of detection line above the walking surface by a desired height and the line of intersection of a walking path of the subject using the assistive walking device.

An exemplary embodiment of the distance sensor mount 134 and first distance sensor 120 is illustrated in FIGS. 3-8. The distance sensor mount 134 includes a body 300 having a length 310. The distance sensor mount 134 provides for adjustment around and along a first axis 340 (FIG. 7) and around and along a second axis 350. Adjustment along the first axis 340 is provided by a telescoping mechanism provided in the body 300 between the first end 360 and the second end 370 opposite the first end 360. The telescoping mechanism adjusts the length 310 of the body 300. As illustrated, the telescoping mechanism is provided by an inner tube 320 disposed in an outer or sheathing tube 330. The inner tube 320 moves into and out of the outer tube 330 and is held in place by a knob 380 and set screw 390 that passes through a threaded opening in the outer tube 330 and presses against the inner tube 320. Other suitable telescoping mechanisms can include external threads on the inner tube 320 and corresponding internal threads on the outer tube 330. The inner tube 320 can include a gear rack and the outer tube 330 can include a corresponding gear wheel. The telescoping mechanism can be manual or motorized.

In addition to providing a telescoping mechanism, the same components of the body 300 can provide a rotation mechanism disposed in the body and configured to permit relative rotation between the first end 360 and the second end 370 of the body 300 around the first axis 340, which is parallel to the length 310 of the body 300. Preferably, the same components that provide for the telescoping mechanism also provide for the rotation mechanism. Alternatively, the telescoping and rotation mechanisms can be separate mechanisms that utilize separate components. The rotation mechanism allows the first distance sensor 120 and therefore the range of detection to rotate about the first axis 340.

Adjustment of the distance sensor mount 134 along the second axis 350 is provided by an attachment mechanism 400 that is disposed on the first end 360 of the body 300 and attached to a selected location on the frame 140 of the assistive walking device 132. In one embodiment, the attachment mechanism 400 includes a mounting body 410 arranged to accept and to accommodate the cross-sectional shaped of the frame 140 of the assistive walking device 132. In general the mounting body 410 partially surrounds the frame 140 and has a gap or opening large enough to allow the frame 140 to pass into and out of the mounting body 410. The attachment mechanism also includes a tightening knob 420 attached to a threaded pin 430 with a rubber tip 440. When the tightening knob 420 is turned, the threaded pin 430 advances into the mounting body 410, clamping the frame 140 between the rubber tip 430 and a plurality of rubber friction pads 250 attached to the inside of the mounting body 410. Reversing the rotation of the tightening knob 420 loosens the clamping on the frame and allows the distance sensor mount to be moved along the frame parallel to the second axis 350.

Other suitable attachment mechanism can be used such as spring loaded clamps and magnetic fasteners. As illustrated, the attachment mechanism 400 is separate from the frame 140 and does not work in conjunction with any components on the frame 140 of the assistive walking device 132, although it is shaped to accommodate the size and shaped of the frame. In another embodiment, the attachment mechanism 400 works in conjunction with structures on the frame 140 including tracks, gear racks, gear wheels, slots and holes.

In one embodiment, the attachment mechanism 400 is directly attached to the first end of the body 300. Alternatively, a pivoting mechanism is provided in the distance sensor mount 134 between the first end 360 of the body 300 and the attachment mechanism 400. The pivoting mechanism 460 provides pivoting or rotational movement of the body 300 around the second axis 350. This also provides rotation between the body 300 and the attachment mechanism 400 as well as rotation of the first distance sensor 120 about the second axis 350.

In one embodiment, the pivoting mechanism includes a first part of a pivot joint 470 extending from the mounting body 410 and a second part of the pivot joint 480 attached to the first end 360 of the body 300. A joint pin 490 passes through aligned holes in the first and second parts of the pivot joint 470. This defines the axis around which the pivoting mechanism pivots. In one embodiment, the joint pin 490 is threaded, and nuts 500, for example wing nuts, are attached to either end of the joint pin 490. The angle between the mounting body 410 and the body 300 is selected and locked in place by tightening the wing nuts 500 on both ends of the joint pin 490. Additional stability is provided by teeth 510 on the first and second parts of the pivot joint.

Figure 8:
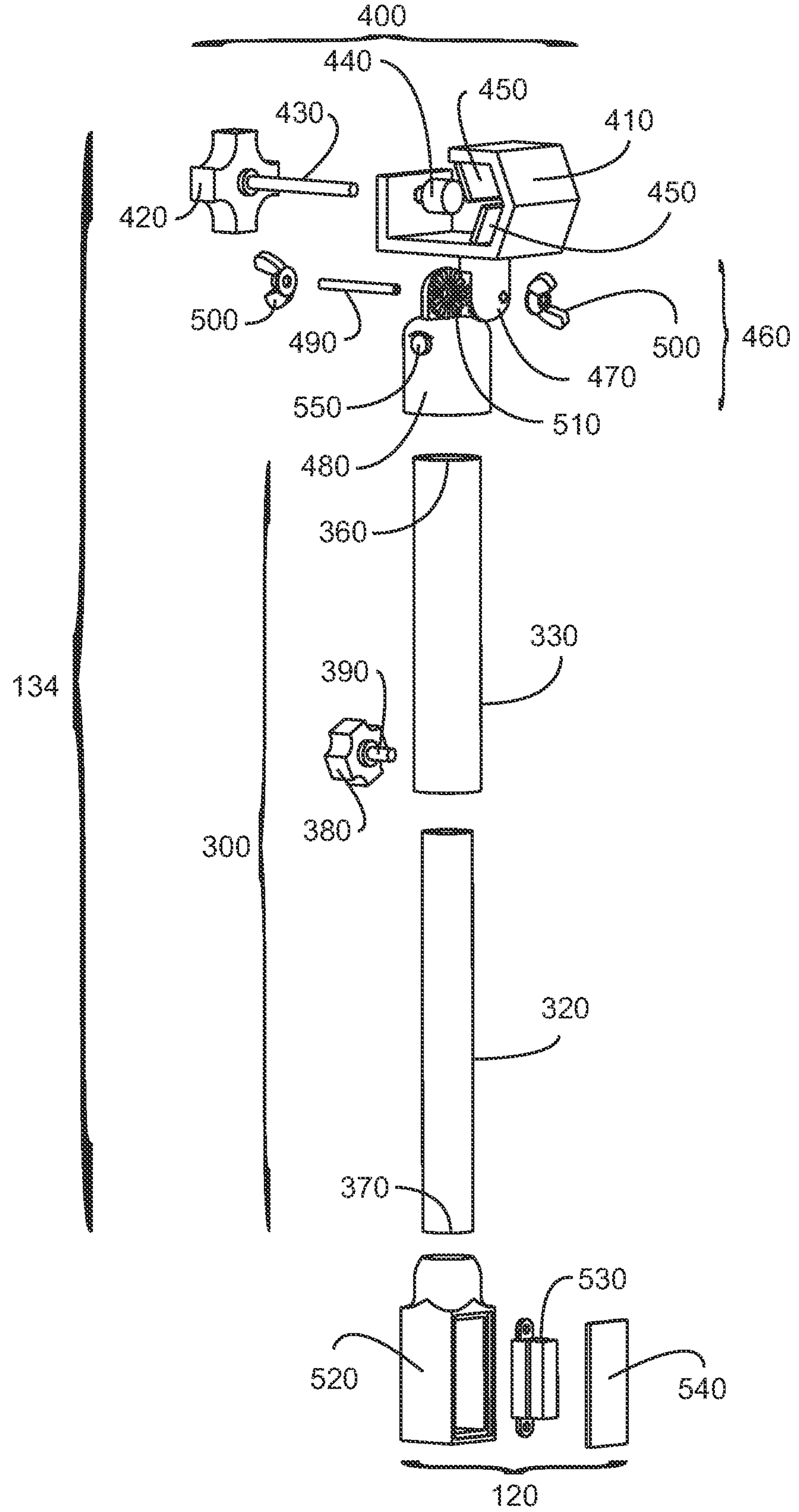
FIG. 8 is an exploded perspective view of the distance sensor mount and distance sensor of FIG. 3.
Figure 9:
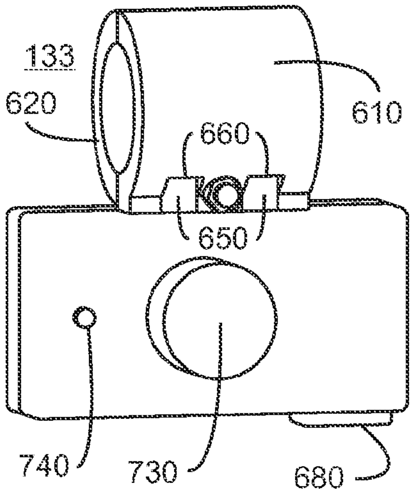
FIG. 9 is a front elevation view of an embodiment of a processing unit for use in accordance with the present invention.
Figure 10:
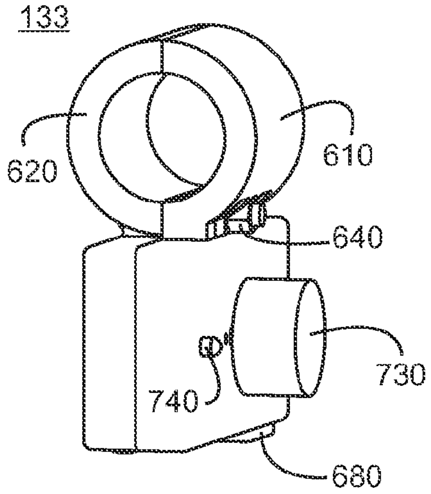
FIG. 10 is a first side elevation view of the processing unit of FIG. 9.
Figure 11:
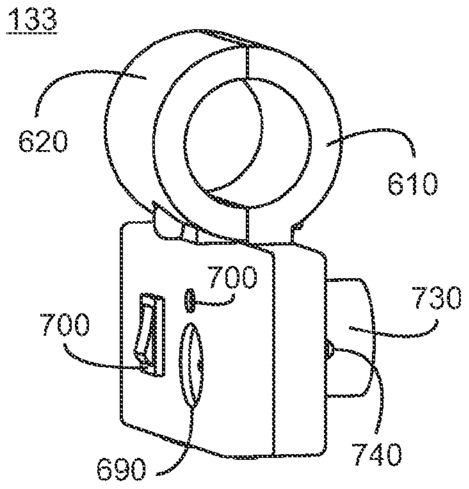
FIG. 11 is a second side elevation view of the processing unit of FIG. 9.
Figure 12:
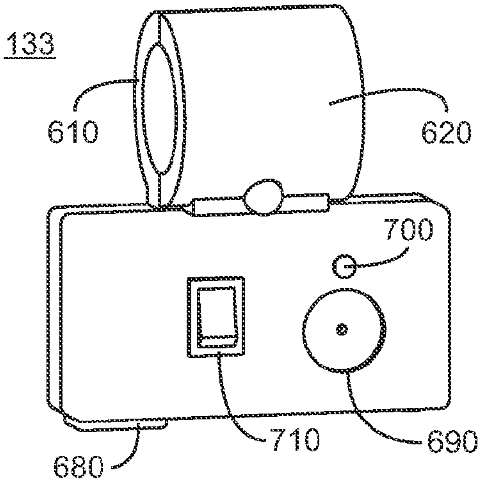
FIG. 12 is a back elevation view of the processing unit of FIG. 9.
Figure 13:
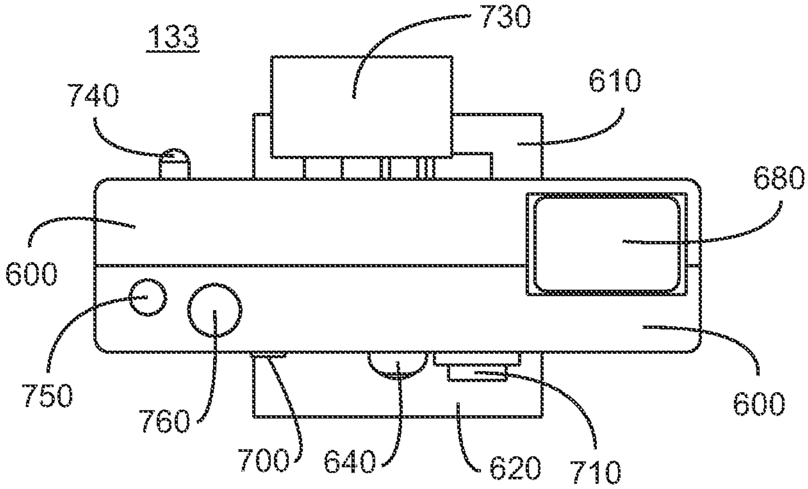
FIG. 13 is bottom plan view of the processing unit of FIG. 9.
Figure 14:
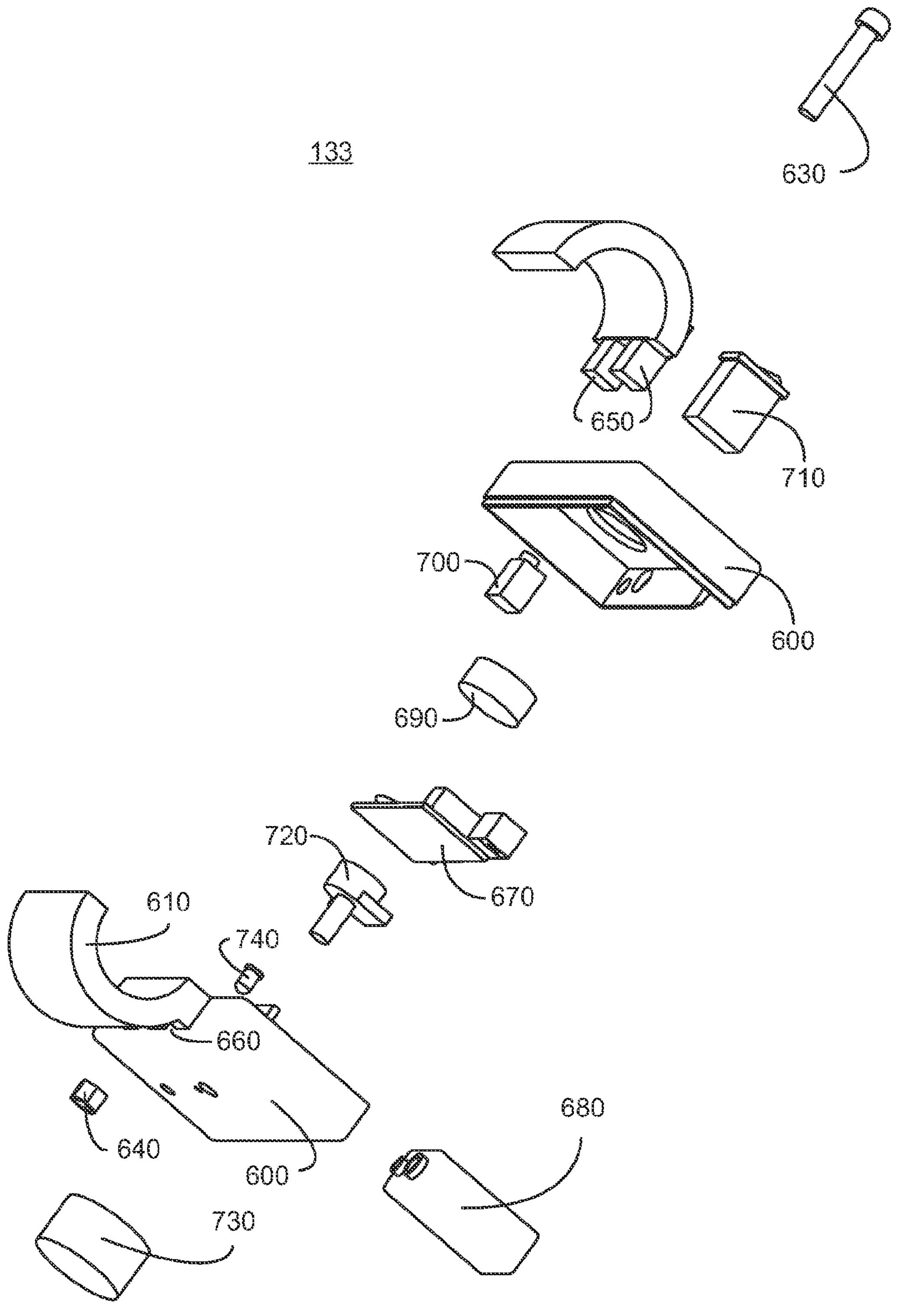
FIG. 14 is an exploded perspective view of the processing unit of FIG. 9.

The first distance sensor 120 is disposed on and attached to the second end 370 of the body. As illustrated in FIG. 8, the first distance sensor 120 includes a sensor enclosure 520 that is attached to bottom of the inner tube 320 and houses the desired sensor components 530 that emit the desired target beam. In one embodiment a bandpass filter lens 540 is mounted on the sensor enclosure 520 to enclose the sensor components. In one embodiment, electric and electronic access to the sensor components is provided by routing the appropriate wires through the body 300. Access to the interior of the body is through the first end 360. In one embodiment, the second part of the pivot joint 480 includes a cable inlet 550 that allows cables (not shown) to enter the pivot joint, run through the body and enter the sensor enclosure 520 to connect to the sensor components 530. The cables permit power and control to be communicated to the sensor components and to collect data from the sensor components. Alternatively, the first distance sensor includes all of the power and control mechanisms. In one embodiment, the first distance sensor communicates wirelessly, e.g., Bluetooth or WiFi, with control and data collection circuits.

The distance sensor mount 134 can be used to attach any sensor to the assistive walking device 132 and provides multiple degrees of freedom of movement of the distance sensor with respect to the assistive walking device.

Returning to FIGS. 1 and 2, the system includes a control or processing unit 133 that is attached to the assistive walking device 132 and is in communication with the distance sensor 120 for example through a wire or cable 136. The processing unit and distance sensor can also communicate wirelessly. The processing unit 133 sends control commands to the distance sensor 120, receives data from the distance sensor 120, analyzes the received data and determines characteristics of the movement of the subject across the walking surface using the analyzed data.

Referring to FIGS. 9-14, an exemplary embodiment of a control box 133 is illustrated. The control box 133 includes a two-piece casing 600. Suitable materials for the casing include, but are not limited to, plastic, metal, wood and other natural or synthetic materials. The control box includes a clamping or attachment mechanism to provide for releasable attachment of the control box 133 to the frame 140 of the assistive walking device 132. In this embodiment, the control box 133 is attached to the frame 140 at a location that is easily accessible to the subject.

In one embodiment as illustrated, the clamping mechanism is a two-part clamping mechanism. The two-part clamping mechanism includes a first attached portion 610 that is attached or fixed to one of the two pieces of the casing 600 and a second independent portion 620. The two parts of the clamping mechanism have complementary mating shapes. The two portions of the clamping mechanism are shaped to fit around the frame 140 of the assistive walking device 132. In one embodiment, each portion of the clamping mechanism represents one half of a cylinder having a circular cross-section. This accommodates a tubular frame. The two portions are secured together and to the frame by tightening a bolt pin 630 and nut 640 that are inserted through both the attached portion of the clamp 610 as well as the independent portion of the clamp 620. In one embodiment, the independent portion 620 includes protrusions 650 that fit into corresponding slots 660 in the first portion 610 to provide for proper alignment of the portions and to strengthen the joint between the portions.

In one embodiment, the processing unit 133 includes circuit board 670 within the casing that includes an analog circuit, a digital circuit, a programmable microprocessor and combinations thereof. These components provide for the desired control of the distance sensors, the collection of data, the processing of this data and the interfacing of the system with the subject. A power source 680, for example a battery, that powers the components on the circuit board 670 and the distance sensor is provided in the casing. Alternatively, the power source can be a rechargeable power source or a photovoltaic power source.

In order to communicate with the subject, the system includes a user interface attached to the assistive walking device and in communication with the processing unit 133. The user interface accepts input from and provides output to the subject. Therefore, the processing unit provides output regarding the determined movement characteristics of the subject through this user interface. For assistive walking devices such as treadmills, the user interface can be incorporated into the control panel of the treadmill. In general, the user interface includes a display, knobs, dials, buttons, switches and combinations thereof. Suitable displays include a light, a printed label, a light emitting diode, a liquid crystal display, a projected image, a computer display and combinations thereof. As illustrated, the user interface is incorporated into the processing unit 133 and includes devices that are in communication with the circuit board 670. These devices include a piezoelectric speaker 690 that actuates audio signal outputs, a stereo audio jack 700 that also actuates audio signal outputs, a knob 730 connected to a potentiometer 720 that controls the volume of audio outputs, a light emitting diode 740 that actuates visual signal outputs, an input jack 750 that receives the cable 136, a sensor calibration dial 760 that adjusts the length range of detection and a switch 710 that toggles the circuit on and off In one embodiment, the system also includes a feedback mechanism attached to the frame of the assistive walking device and is in communication with the processing unit. The feedback mechanism communicates the determined movement characteristics to the subject. In one embodiment, the components of the processing unit 133 are used as the feedback mechanism. Suitable feedback mechanisms include, but are not limited to, tactile feedback, visual feedback, auditory feedback and combinations thereof. For example, the tactile feedback can be vibration, created by an spinning eccentric weight location in the processing unit and communicating the vibration through the frame. The visual feedback can be a light, a gauge, a computer readout, a light emitting diode display, a liquid crystal display, a projected image, a paper printout, a computer display and combinations thereof. For example, the display of a treadmill can be used or the lights associated with the processing unit. Suitable auditory feedback includes, but is not limited to, a tone, a series of tones, a melody, a synthesized voice, a recorded voice and combinations thereof. These can use the speaker and speaker jack of the processing unit.

Figure 16:
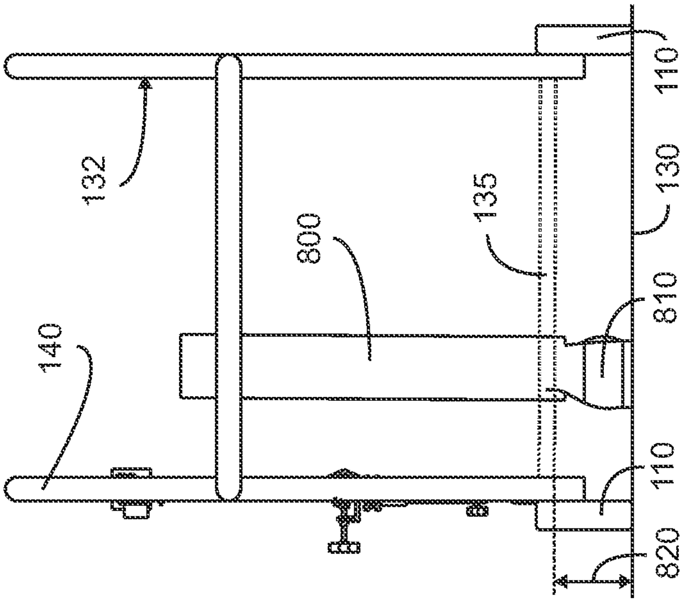
FIG. 16 is a front elevation view of an embodiment of the assistive walking device of the present invention with a subject's foot under the range of detection of the distance sensor.
Figure 20:
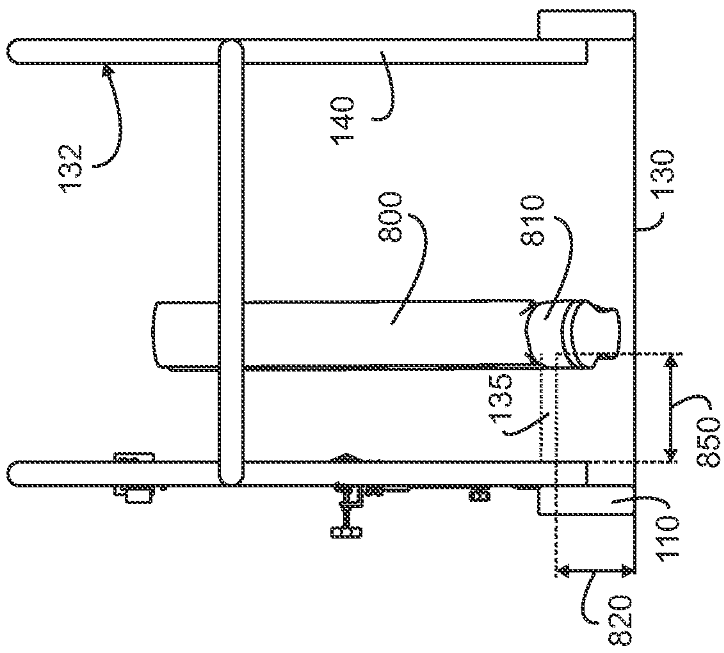
FIG. 20 is a front elevation view of an embodiment of the assistive walking device of the present invention with a subject's foot crossing the range of detection of the distance sensor using a heel-toe motion.

The present invention is also directed to a method for improving movement in a subject using the system of the present invention. The first distance sensor 120, or any other distance sensor in accordance with the present invention, is associated with the assistive walking device 132 by attaching the distance sensor mount 134 to the frame 140. The first distance sensor is used to detect a portion, e.g., the foot, of the subject crossing into the range of detection of the first distance sensor that extends along the first line running from the first distance sensor. In addition, the first distance sensor determines a distance from that portion of the subject to the distance sensor. Referring to FIGS. 15-20, the portion of the subject can be the leg 800 or foot 810 of the subject using the assistive walking device 132. As shown in FIGS. 16 and 20, the line of the range of detection 135 of the first distance sensor is spaced a desired height 820 above the walking surface 130. This height 820 can be selected to be close enough to the walking surface 130 such that any step of the subject intersects the line 135.

Figure 15:
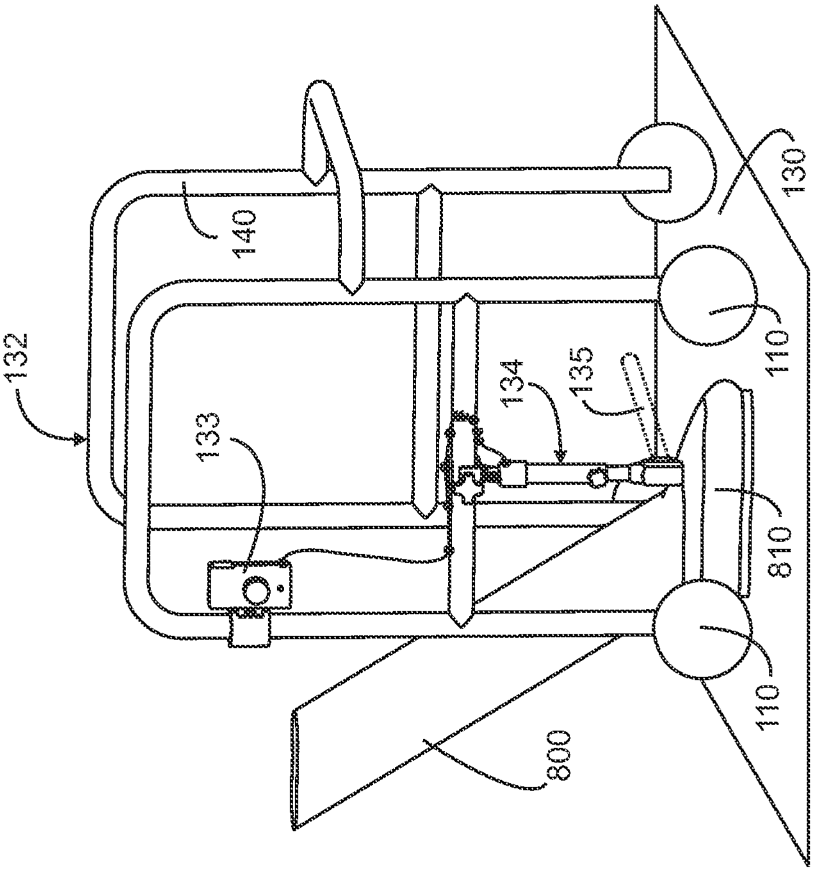
FIG. 15 is a perspective view of an embodiment of the assistive walking device of the present invention with a subject's foot under the range of detection of the distance sensor.
Figure 17:
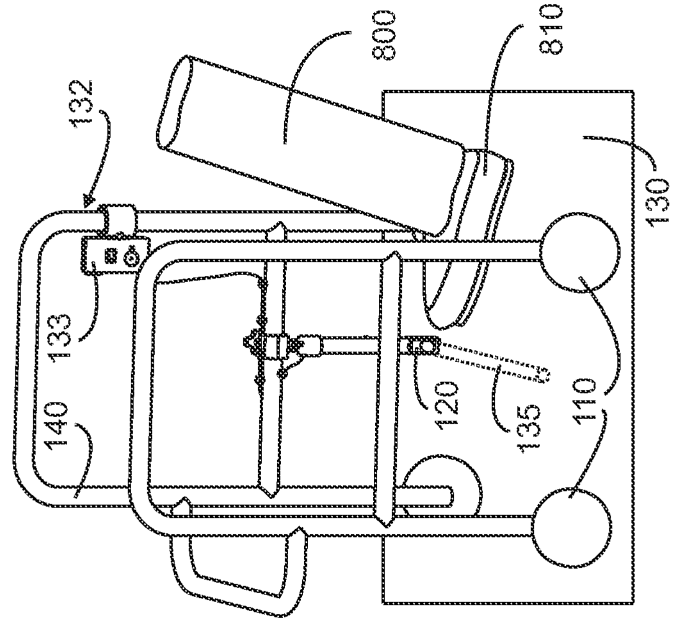
FIG. 17 is a perspective view of an embodiment of the assistive walking device of the present invention with a subject's foot making a heel-toe motion.

Alternatively, the line 135 is spaced above the walking surface 130 a sufficient distance to encourage the subject to make the proper walking motion. As illustrated in FIGS. 15 and 16, the line 135 is spaced a height 820 above the walking surface such that the foot 810 of the subject will pass beneath the line 135 when the subject makes a shuffling motion with the foot 810, i.e., sliding the foot 810 along the walking surface 130 without significantly raising the heel or toe. As the foot does not intersect the line of the first distance sensor, the subject is not provided with any positive feedback, because the selected illustrated height 820 is selected to encourage the subject to walk with a heel-to-toe motion, raising the toe of the foot 810 above of the walking surface as illustrated in FIG. 17.

Figure 18:
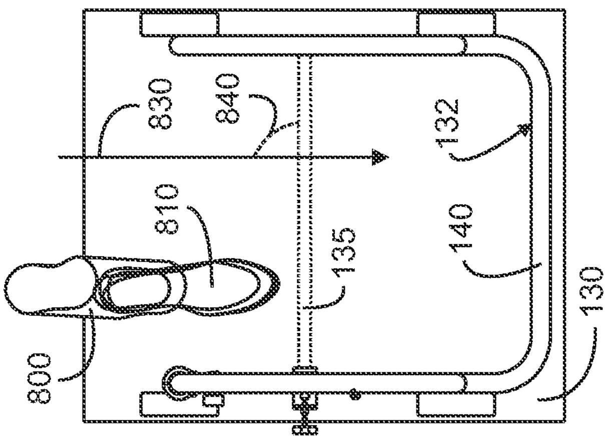
FIG. 18 is a top plan view of an embodiment of the assistive walking device of the present invention with a subject's foot moving perpendicular to the range of detection of the distance sensor.
Figure 19:
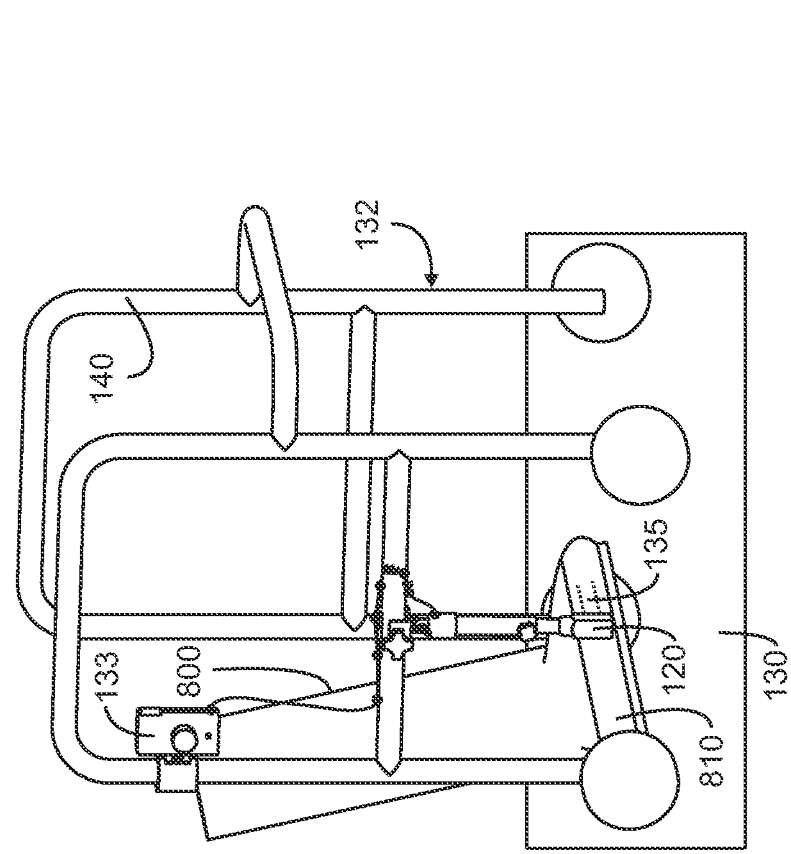
FIG. 19 is a perspective view of an embodiment of the assistive walking device of the present invention with a subject's foot crossing the range of detection of the distance sensor using a heel-toe motion.

Referring to FIGS. 19 and 20, the toe of the foot 810 intersects the line of the range of detection 135 when the foot is moved using the heel-to-toe motion a sufficient distance. This triggers a positive feedback response being delivered to the subject. The first distance sensor detects the foot in the line of detection and can also determine a distance 850 between the first distance sensor and that foot 810. As illustrated in FIG. 18, the various adjustments in the distance sensor mount, in addition to providing for height adjustment, allow the line of the range of detection 135 to be moved parallel to the line of movement 830 of the subject's leg 800 and foot 810. In addition, the line of the range of detection 135 can be pivoted to adjust the angle 840 between the line of the range of detection 135 and the line of movement 830. All of these adjustments provide for different scenarios to be used in evaluating and improving the movement of a subject using the assistive walking device. Depending on the position, the system can target stride length, gait, pace, cadence, lateral wavering and gait symmetry.

In one embodiment, the portion of the subject to be detected is the foot of the subject, and the first line 135 is positioned above the walking surface 130 a sufficient distance so that each foot of the subject crosses into the range of detection only when the subject moves by foot across the walking surface using a heel-to-toe walking motion. Alternatively, the portion of the subject to be detected is a foot of the subject, and the first line is positioned a sufficient distance from the subject moving by foot across the walking surface using the assistive walking device so that each foot of the subject crosses into the range of detection only when the subject moves by foot across the walking surface using a prescribed stride length. In one embodiment, a time required for the subject to repeatedly move each foot into the range of detection is measured and used to determine a pace for the subject at the prescribed stride length. Feedback is provided to the subject regarding the determined pace such that this feedback can be used to modify the determined pace of the subject.

In one embodiment, the portion of the subject to be detected is a foot of the subject, and the first line is positioned above the walking surface a distance so that each foot of the subject crosses into the range of detection upon any given stride, regardless of stride length or heel-to-toe motion. A time required for the subject to repeatedly move each foot into the range of detection is measured and used to determine a cadence for the subject. Feedback is provided to the subject regarding the determined cadence and is used to modify the determined cadence of the subject.

In one embodiment, the portion of the subject to be detected is the foot of the subject, and for each foot changes in a gait distance between that foot and the first distance sensor between successive strides of each foot is tracked. These tracked changes are used to determine lateral wavering for each foot. Feedback is provided to the subject regarding the determined lateral wavering, and the feedback is used to modify the lateral wavering of each foot of the subject.

In one embodiment, the portion of the subject to be detected is a foot of the subject, and for each foot a gait distance between that foot and the first distance sensor during successive strides of each foot is tracked. The tracked gait distances of both feet are compared to determine a gait symmetry. Feedback is provided to the subject regarding the determined gait symmetry and is used to modify the gait symmetry of the subject. In general, feedback is provided to the subject regarding detection of the desired portion of the subject crossing into the range of detection in addition to the determined distance, and this feedback is used to improve movement in the subject.

In one embodiment, a plurality of additional distance sensors is associated with the assistive walking device, and each additional distance sensor is used to detect a distinct portion of the subject crossing into a range of detection of that additional distance sensor. These ranges of detection extend along an additional lines running from each additional distance sensor. In addition, each additional sensor is used to determine a distance from the distinct portion of the subject crossing into the range of detection and the additional distance sensor.

In one embodiment, by employing the auditory and visual feedback of the invention, subjects are trained to increase their stride lengths and walk with a heel-toe motion as a means of recalibrating proprioceptive feedback from their leg muscles and thus correct the sensory-motor mismatch in a similar way as it seems to do in the Lee Silverman Voice Treatment program (Ramig, Intelligibility in Speech Disorders: Theory, Measurement and Management, John Benjamins Pub. Co., R. Kent, ed., Amsterdam, 1992). This embodiment may be implemented for subjects with neurodegenerative conditions and movement disorders such as but not limited to Parkinson's Disease, Parkinsonian syndromes, Senile Gait Disorder, and Ataxia; all of which are capable of inducing sensory-motor mismatch.

In another implementation, the auditory and visual feedback of the invention can supplement or substitute the feedback usually provided by a trainer, therapist, caretaker, or variation thereof during the course of physical rehabilitation following injury or surgery. The invention is used outside of physical therapy sessions to reinforce the feedback given by therapists during therapeutic sessions. Therapists adjust the gait training system to provide the subject with positive feedback when desired gait characteristics are detected. Depending on the injury, these characteristics may include a minimum stride length to increase range of motion in the leg joints, a heel-toe motion to maximize stability, symmetry between the left and right leg to promote proper weight distribution, and the like. The gait training system in this implement likely, but does not necessarily, incorporates the use of a walker, rollator, or cane as the assistive walking device.

In another implementation, the auditory and visual feedback of the invention can supplement or substitute the feedback usually provided by a trainer, coach, or variation thereof during the course of athletic training such as walking, jogging, running, or variations thereof The invention is used during training sessions to provide real-time feedback of gait characteristics to subjects. Subjects themselves or their trainers may set up the invention to detect desired characteristics such as cadence, pace, stride length, symmetry, heel-toe motion, and the like. The gait training system in this implement likely, but does not necessarily, involve the subject walking, jogging, or running upon a treadmill to which the gait training system is attached.

In another implementation, the auditory and visual feedback of the invention can supplement or substitute the feedback usually provided by a trainer in the process of training a subject to walk, jog, or run, with certain gait characteristics. These characteristics may include a specific stride length, symmetry, cadence, pace, and the like. Subjects in this implementation are animals, such as dogs and horses. In this case, the animal must first be conditioned to associate the auditory feedback such as a tone of a certain frequency or the visual feedback such as the illumination of a certain light with a favorable event. This is achieved by repeatedly pairing the presentation of the feedback intended for use with the invention with the presentation of enjoyable stimuli, such as food, petting, or verbal praise. The aforementioned procedure, called Pavlovian conditioning, is a well established methodology. After successful conditioning, the animal will eventually perceive said feedback intended for use with the invention as a desirable event, and the gait training system may be used. The gait training system in this implement likely, but does not necessarily, involve the subject walking, jogging, or running upon a treadmill to which the gait training system is attached.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are incorporated by reference in their entirety.

What is claimed is:

1. A system for improving movement in a subject, the system comprising:

an assistive walking device comprising a frame extending up from a walking surface, the frame configured to support the subject moving by foot across the walking surface;

a first distance sensor attached to the frame of the assistive walking device, the distance sensor comprising a range of detection extending along a first straight line running from the frame across the walking surface a constant distance above the walking surface, the distance sensor configured to detect an object crossing into the first line within the range of detection and to determine a distance from that object to the distance sensor; and a processing unit attached to the assistive walking device, communicating with the first distance sensor, receiving data from the first distance sensor indicating the object crossing into the first line and the distance from the object to the distance sensor and using the data to determine characteristics of a gait the subject, the characteristics comprising stride length along the walking surface and lateral variability of the gait along the first straight line.

2. The system of claim 1, wherein the assistive walking device comprises a walker.

3. The system of claim 1, wherein the assistance walking device comprises a treadmill and the walking surface comprises a moving treadmill surface of the treadmill.

4. The system of claim 1, wherein the distance sensor comprises an optoelectronic distance sensing device comprising:

an optical light source emitting a pre-defined frequency of light along the first line; and a photodetector filtered to detect the pre-defined frequency.

5. The system of claim 4, wherein the optoelectronic distance sensing device further comprises a timing device in communication with the optical light source and photodetector, the timing device configured to measure an elapsed time for light of the pre-defined frequency to project from the optical light source along the first line, to reflect on the object crossing into the first line and to fall upon the photodetector.

6. The system of claim 5, wherein the pre-defined frequency is from about 1 mm to about 750 nm.

7. The system of claim 1, wherein the distance sensor comprises a sonic-electric distance sensing device comprising:

a cyclic sound pressure generator emitting a pre-defined frequency of sound along the first line; and a sonic detector configured to detect the pre-defined frequency of sound.

8. The system of claim 7, wherein the sonic-electric distance sensing device further comprises a timing device in communication with the cyclic sound pressure generator and the sonic detector, the timing device configured to measure an elapsed time for sound of the pre-defined frequency to project from the cyclic sound pressure generator, to reflect on the object crossing into the first line and to fall upon the sonic detector.

9. The system of claim 8, wherein the pre-defined frequency is at least about 20 kHz.

10. The system of claim 1, wherein the distance sensor comprises a radio detection and ranging device comprising:

a radio transmitter emitting a pre-defined frequency of radiation along the first line; and a radio receiver configured to detect the pre-defined frequency of radiation.

11. The system of claim 10, wherein the radio detection and ranging device further comprises a timing device in communication with the radio transmitter and the radio receiver, the timing device configured to measure an elapsed time for radiation of the pre-defined frequency to project from the radio transmitter, to reflect on the object crossing the first line and to fall upon the radio receiver.

12. The system of claim 1, further comprising a second distance sensor separate from the first distance sensor and attached to the frame of the assistive walking device and comprising a second range of detection extending along a second straight line running from the frame across the walking surface a constant distance above the walking surface, the second line separate from and parallel to the first line and the second distance sensor configured to detect an object crossing into the second line within the range of detection and to determine a distance from that object to the second distance sensor.

13. The system of claim 12, wherein the first distance sensor and the second distance sensor comprise a unitary structure.

14. The system of claim 12, wherein the first distance sensor and the second distance sensor comprise different types of distance sensors.

15. The system of claim 12, wherein the first distance sensor and the second distance sensor comprise the same type of distance sensor.

16. The system of claim 1, wherein the first line is spaced above the walking surface a desired height and intersects a walking path of the subject using the assistive walking device.

17. The system of claim 1, further comprising a distance sensor mount attached to the frame of the assistive walking device, the distance sensor mount comprising:

a body having a length;

an attachment mechanism disposed on a first end of the body and attached to a selected location on the frame of the assistive walking device;

a second end opposite the first end, the first distance sensor disposed on the second end;

and a telescoping mechanism disposed in the body between the first and second ends and configured to adjust the length of the body.

18. The system of claim 17, wherein the distance sensor mount further comprises a rotation mechanism disposed in the body and configured to permit relative rotation between the first end and the second end of the body around an axis parallel to the length of the body.

19. The system of claim 17, wherein the distance sensor mount further comprises a pivoting mechanism disposed between the body and the attachment mechanism, the pivoting mechanism configured to facilitate pivoting movement between the body and the attachment mechanism.

20. The system of claim 1, wherein the processing unit is configured to send control commands to the distance sensor.

21. The system of claim 1, wherein the processing unit comprises an analog circuit, a programmable microprocessor or combinations thereof.

22. The system of claim 1, further comprising a user interface to the assistive walking device and in communication with the processing unit, the user interface configured to accept input from and provide output to the subject, the processing unit configured to provide output regarding the determined movement characteristics through the user interface.

23. The system of claim 22, wherein the user interface comprises a display, knobs, dials, buttons, switches or combination thereof.

24. The system of claim 23, wherein the display comprises a light, a printed label, a light emitting diode, a liquid crystal display, a projected image, a computer display or combinations thereof.

25. The system of claim 1, further comprising a feedback mechanism attached to the assistive walking device and in communication with the processing unit, the feedback mechanism configured to communicate the determined movement characteristics to the subject.

26. The system of claim 25, wherein the feedback mechanism comprises tactile feedback, visual feedback, auditory feedback or combinations thereof.

27. The system of claim 26, wherein the tactile feedback comprises vibration.

28. The system of claim 26, wherein the visual feedback comprises a light, a gauge, a computer readout, a light emitting diode display, a liquid crystal display, a projected image, a paper printout, a computer display or combinations thereof.

29. The system of claim 26, wherein the auditory feedback comprises a tone, a series of tones, a melody, a synthesized voice, a recorded voice or combinations thereof.

* * * * *